(12) United States Patent
Stirton et al.

(10) Patent No.: US 6,643,008 B1
(45) Date of Patent: Nov. 4, 2003

(54) METHOD OF DETECTING DEGRADATION IN PHOTOLITHOGRAPHY PROCESSES BASED UPON SCATTEROMETRIC MEASUREMENTS OF GRATING STRUCTURES, AND A DEVICE COMPRISING SUCH STRUCTURES

(75) Inventors: James Broc Stirton, Austin, TX (US); Kevin R. Lensing, Austin, TX (US)

(73) Assignee: Advanced Micro Devices, Inc., Austin, TX (US)

(*) Notice: Subject to any disclaimer, the term of this patent is extended or adjusted under 35 U.S.C. 154(b) by 0 days.

(21) Appl. No.: 10/083,699

(22) Filed: Feb. 26, 2002

(51) Int. Cl.[7] ............................................... G01N 21/00
(52) U.S. Cl. ..................... 356/237.5; 356/394; 438/14; 438/16; 430/30
(58) Field of Search .......................... 356/237.1–237.6, 356/388, 392, 394; 250/492.3, 492.2, 492.22, 492.1; 430/290, 311, 30.5; 438/14–16

(56) References Cited

U.S. PATENT DOCUMENTS

| | | | | |
|---|---|---|---|---|
| 5,279,924 A | * | 1/1994 | Sakai et al. | 430/290 |
| 5,343,292 A | * | 8/1994 | Brueck et al. | 356/363 |
| 5,415,835 A | * | 5/1995 | Brueck et al. | 430/311 |
| 5,585,211 A | * | 12/1996 | Firstein et al. | 250/492.3 |
| 5,867,276 A | | 2/1999 | McNeil et al. | 356/445 |
| 5,877,860 A | | 3/1999 | Borden | 356/376 |
| 5,880,838 A | | 3/1999 | Marx et al. | 356/351 |
| 5,963,329 A | * | 10/1999 | Conrad et al. | 356/372.5 |
| 6,051,348 A | | 4/2000 | Marinaro et al. | 430/30 |
| 6,081,334 A | | 6/2000 | Grimbergen et al. | 356/357 |
| 6,245,584 B1 | | 6/2001 | Marinaro et al. | 438/14 |
| 6,383,824 B1 | * | 5/2002 | Lensing | 356/445 |
| 6,433,878 B1 | * | 8/2002 | Niu et al. | 356/394 |
| 6,448,097 B1 | * | 9/2002 | Singh et al. | 250/492.22 |
| 6,479,200 B1 | * | 11/2002 | Stirton | 430/30 |
| 6,483,580 B1 | * | 11/2002 | Xu et al. | 356/300 |
| 2002/0135781 A1 | | 9/2002 | Singh et al | 356/601 |

* cited by examiner

Primary Examiner—Frank G. Font
Assistant Examiner—Sang H. Nguyen
(74) Attorney, Agent, or Firm—Williams, Morgan & Amerson, P.C.

(57) ABSTRACT

The present invention is generally directed to various methods of detecting degradation in photolithography processes based upon scatterometric measurements of grating structures, and a device comprising such structures. In one embodiment, the method comprises providing a wafer comprised of a plurality of grating structures, each of the grating structures being comprised of a plurality of features, each of the grating structures having a different critical dimension, illuminating at least one of the grating structures, measuring light reflected off of at least one of the grating structures to generate an optical characteristic trace for the grating structure, and determining the presence of residual photoresist material between the features of the grating structure by comparing the generated optical characteristic trace to at least one optical characteristic trace from a library. In some embodiments, the grating structures are arranged in a linear array. In one illustrative embodiment, the device comprises a wafer and a plurality of grating structures formed above the wafer, each of the grating structures having a different critical dimension, and at least one of the grating structures having a critical dimension that is less than an anticipated range of critical dimensions for integrated circuit devices to be formed on a wafer.

46 Claims, 5 Drawing Sheets

(Prior Art)

METHOD OF DETECTING DEGRADATION IN PHOTOLITHOGRAPHY PROCESSES BASED UPON SCATTEROMETRIC MEASUREMENTS OF GRATING STRUCTURES, AND A DEVICE COMPRISING SUCH STRUCTURES

BACKGROUND OF THE INVENTION

1. Field of the Invention

This invention relates generally to semiconductor fabrication technology, and, more particularly, to a method of detecting degradation in photolithography processes based upon scatterometric measurements of grating structures, and a device comprising such structures.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

Figure 1:
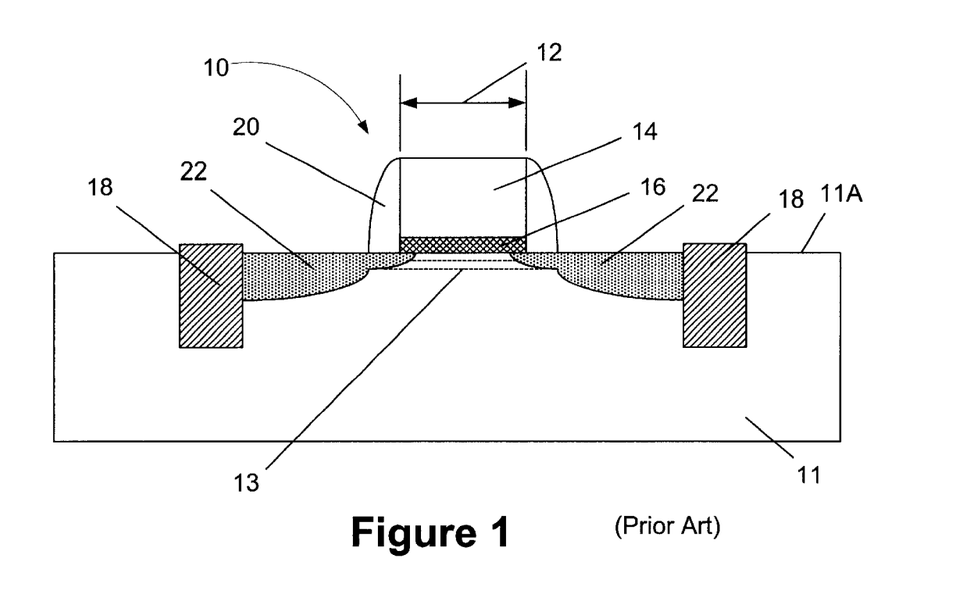
FIG. 1 is a cross-sectional view of an illustrative prior art transistor.

By way of background, an illustrative field effect transistor 10, as shown in FIG. 1, may be formed above a surface 11A of a semiconducting substrate or wafer 11 comprised of doped-silicon. In the process of forming integrated circuit devices, millions of transistors, such as the illustrative transistor 10 depicted in FIG. 1, are formed above a semiconducting substrate. The substrate 11 may be doped with either N-type or P-type dopant materials, for example. The transistor 10 may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit device is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

The gate electrode 14 has a critical dimension 12, i.e., the width of the gate electrode 14, that approximately corresponds to the channel length 13 of the device when the transistor is operational. Of course, the critical dimension 12 of the gate electrode 14 is but one example of a feature that must be formed very accurately in modern semiconductor manufacturing operations. Other examples include, but are not limited to, conductive lines, openings in insulating layers to allow subsequent formation of a conductive interconnection, i.e., a conductive line or contact, therein, etc.

During the course of fabricating such integrated circuit devices, a variety of features, e.g., gate electrodes, conductive lines, openings in layers of insulating material, etc., are formed to very precisely controlled dimensions. Such dimensions are sometimes referred to as the critical dimension (CD) of the feature. It is very important in modem semiconductor processing that features be formed as accurately as possible due to the reduced size of those features in such modem devices. For example, gate electrodes may now be patterned to a width 12 that is approximately 0.18 $\mu$m (1800 Å), and further reductions are planned in the future. As stated previously, the width 12 of the gate electrode 14 corresponds approximately to the channel length 13 of the transistor 10 when it is operational. Thus, even slight variations in the actual dimension of the feature as fabricated may adversely affect device performance. Thus, there is a great desire for a method that may be used to accurately, reliably and repeatedly form features to their desired critical dimension, i.e., to form the gate electrode 14 to its desired critical dimension 12.

Photolithography is a process typically employed in semiconductor manufacturing. Photolithography generally involves forming a layer of photoresist material (positive or negative) above one or more layers of material, e.g., polysilicon, silicon dioxide, etc., that are desired to be patterned. Thereafter, a pattern that is desired to be formed in the underlying layer or layers of material is initially formed in the layer of photoresist using an appropriate stepper tool and known photolithographic techniques, i.e., an image on a reticle in the stepper tool is transferred to the layer of photoresist. Then, the layer of photoresist is developed so as to leave in place a patterned layer of photoresist substantially corresponding to the pattern on the reticle. This patterned layer of photoresist is then used as a mask in subsequent etching processes, wet or dry, performed on the underlying layer or layers of material, e.g., a layer of polysilicon, metal or insulating material, to transfer the desired pattern to the underlying layer. The patterned layer of photoresist is comprised of a plurality of features, e.g., line-type features or opening-type features, that are to be replicated in an underlying process layer. The features in the patterned layer of photoresist also have a critical dimension, sometimes referred to as a develop inspect critical dimension (DICD).

More particularly, in one illustrative embodiment, modern photolithography processes generally involve the steps of: (1) applying a layer of photoresist above a wafer, typically accomplished by a spin-coating process; (2) pre-baking (or soft-baking) the layer of photoresist at a temperature of approximately 90–120° C. to reduce the level of solvents in the layer of photoresist and to improve the adhesion characteristics of the photoresist; (3) performing an exposure process, wherein a pattern is projected onto the layer of photoresist through a reticle used in a stepper tool to create a latent image in the layer of photoresist; (4) performing a post-exposure bake on the layer of photoresist at a temperature approximately 5–15° C. higher than the pre-bake process; (5) performing a develop process to turn the latent image in the layer of photoresist into the final resist image; and (6) performing a postbake process (or hard-bake) at a temperature of approximately 125–160° C. to remove residual solids, improve adhesion, and to increase the etch resistance of the photoresist. These process steps are well known to those skilled in the art and, thus, will not be described herein in any greater detail.

Figure 2A:
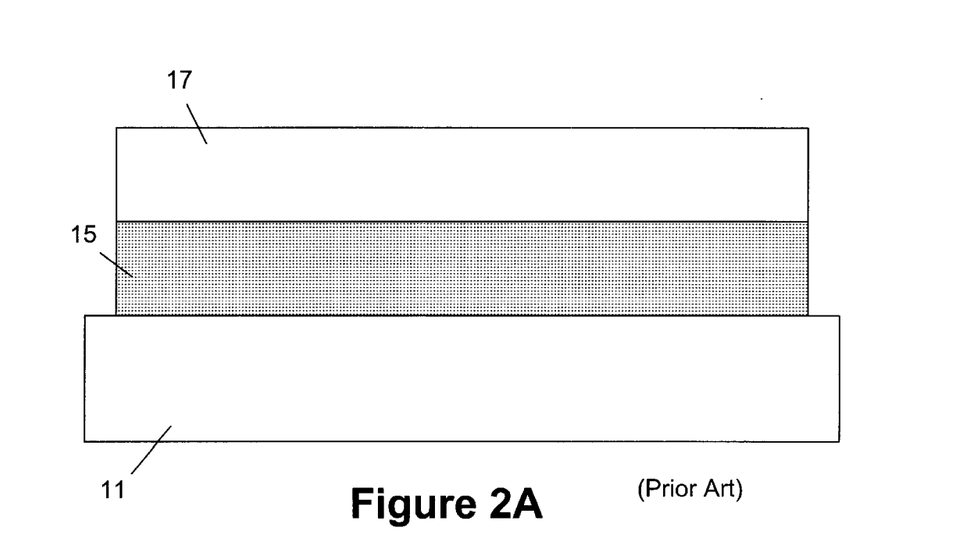
FIGS. 2A–2B are cross-sectional views of a process layer having a layer of photoresist formed thereabove.
Figure 2B:
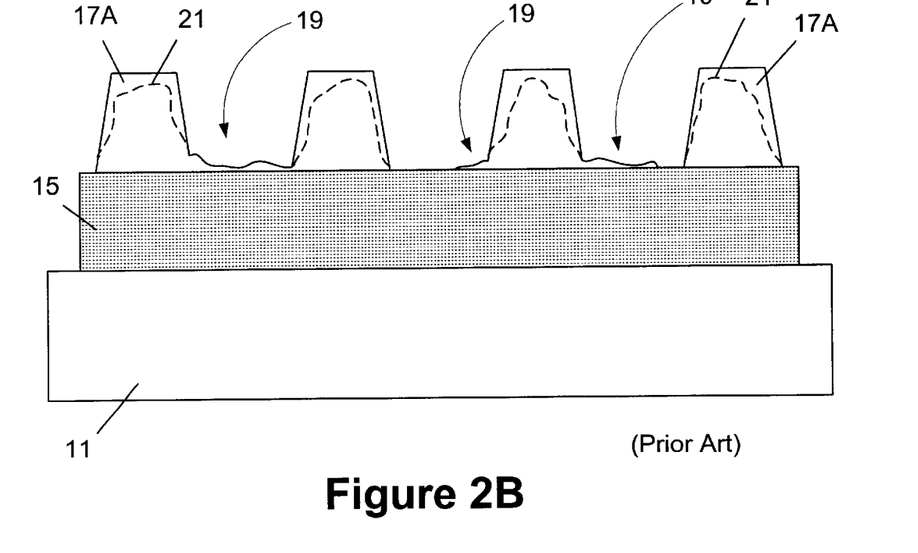

Further background for the present invention will now be described with reference to FIGS. 2A–2B. As shown in FIG. 2A, a process layer 15 is formed above a semiconducting substrate 11 (or other previously-formed process layer), and a layer of photoresist material (positive or negative) 17 is formed above the process layer 15. The process layer 15 is meant to be illustrative of any type of material that may be patterned using known photolithographic and etching techniques.

Using known photolithographic techniques, the layer of photoresist material 17 is patterned to define a plurality of photoresist features 17A that are intended to be used as a mask in patterning the underlying process layer 15. See FIG. 2B. However, for a variety of reasons, the photolithography process may be incomplete and result in residual amounts of photoresist material 19 remaining between the photoresist features 17A. In the industry, this situation is sometimes referred to as photoresist "scumming." Such scumming may be the result of a variety of factors, e.g., low stepper exposure dose, improper focus, insufficient develop time, etc. Additionally, the profile of the features 17A may also be degraded, as indicated by the dashed lines 21 in FIG. 2B, as part of the scumming phenomenon. Moreover, the degree of photoresist scumming may vary, e.g., the photoresist material between the features 17A may be partially removed to expose portions of the underlying process layer 15, or scumming may be so severe that the underlying process layer 15 is not exposed between the features 17A.

Photoresist scumming can cause many problems in subsequent manufacturing operations. For example, the ability to completely etch the underlying process layer 15 may be hampered due to the presence of the residual photoresist material 19, i.e., etching of the process layer 15 may be incomplete. As a result, device performance may be adversely impacted, and/or wafers may have to be re-worked to correct problems caused by photoresist scumming. Moreover, photoresist scumming becomes even more problematic as device feature sizes continue to decrease (with resulting increased density). That is, as device features continue to decrease and packing density continues to increase, photoresist scumming is more likely to occur. Lastly, photoresist scumming may not be uniform across the entire surface of the wafer, i.e., scumming may only occur in certain areas of the wafer.

The present invention is directed to a method and device that may solve, or at least reduce, some or all of the aforementioned problems.

SUMMARY OF THE INVENTION

The present invention is generally directed to various methods of detecting degradation in photolithography processes based upon scatterometric measurements of grating structures, and a device comprising such structures. In one illustrative embodiment, the method comprises providing a wafer comprised of a plurality of grating structures, each of the grating structures being comprised of a plurality of features, each of the grating structures having a different critical dimension, illuminating at least one of the grating structures, measuring light reflected off of at least one of the grating structures to generate an optical characteristic trace for the grating structure, and determining the presence of residual photoresist material between the features of the grating structure by comparing the generated optical characteristic trace to at least one optical characteristic trace from a library. In some embodiments, the grating structures are arranged in a linear array. In further embodiments, at least one and, in some cases, a plurality of grating structures have a critical dimension that is less than an anticipated range of critical dimensions for integrated circuit devices to be formed on a wafer.

In another illustrative embodiment, the method comprises providing a wafer comprised of a plurality of grating structures, each of the grating structures being comprised of a plurality of spaced-apart photoresist features, each of the grating structures having a different spacing between the photoresist features, at least one of the grating structures having a spacing between the photoresist features that is less than an anticipated range of critical dimensions for integrated circuit devices to be formed on a wafer, illuminating at least one of the plurality of grating structures, measuring light reflected off of at least one of the grating structures to generate an optical characteristic trace for the at least one grating structure, and determining the presence of residual photoresist material between the features of the at least one grating structure by comparing the generated optical characteristic trace to at least one optical characteristic trace from a library.

In a further embodiment, the device comprises a wafer and a plurality of grating structures formed above the wafer, each of the grating structures having a different critical dimension, and at least one of the grating structures having a critical dimension that is less than an anticipated range of critical dimensions for integrated circuit devices to be formed on a wafer.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to various methods of detecting degradation in photolithography processes based upon scatterometric measurements of grating structures, and a device comprising such structures. As will be readily apparent to those skilled in the art upon a complete reading of the present application, the present method is applicable to a variety of technologies, e.g., NMOS, PMOS, CMOS, etc., and it is readily applicable to a variety of devices, including, but not limited to, logic devices, memory devices, etc.

Figure 3:
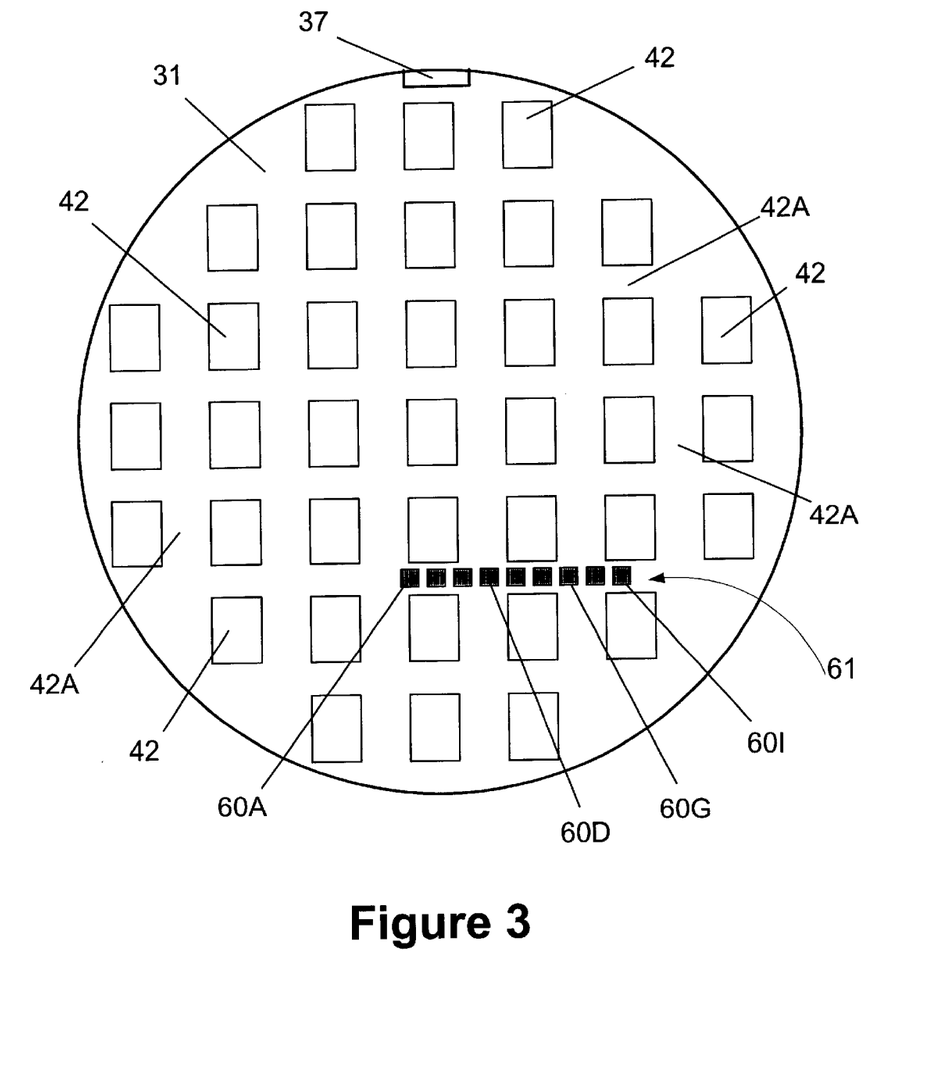
FIG. 3 is a plan view of an illustrative wafer depicting several production die and a plurality of grating structures formed above said wafer.

As shown in FIG. 3, a plurality of production die 42 are formed above a wafer 31. The die 42 define an area of the wafer 31 where production integrated circuit devices, e.g., microprocessors, ASICs, memory devices, etc., will be formed. The size, shape and number of die 42 per wafer 31 depend upon the type of device under construction. For example, several hundred die 42 may be formed above an 8-inch diameter wafer 31. The production die 42 are separated from each other by scribe lines 42A. After the fabrication processes are completed, the wafer 31 will be cut along the scribe lines 42A, and the production die 42, containing the integrated circuit device formed thereon, will be packaged and sold. The wafer 31 may also have an alignment notch 37 that is used to provide relatively rough alignment of the wafer 31 prior to performing certain processes, e.g., an exposure process in a stepper tool.

Also depicted in FIG. 3 is an illustrative array 61 of a plurality of grating structures 60A–I formed above the wafer 31. For ease of reference, the grating structures 60A–I may be referred to individually and/or collectively by the reference numeral 60. As will be recognized by those skilled in the art after a complete reading of the present application, the size, shape, number, location and orientation of the grating structures 60 may be varied as a matter of design choice. Moreover, although the illustrative grating structures 60A–I are depicted in a linear array, they may be oriented in a different manner, or individually dispersed around the surface of the wafer 31 in a random manner. The grating structures 60 may be formed in the scribe lines 42A, or in the production die 42, assuming enough plot space is available.

Figure 4A:
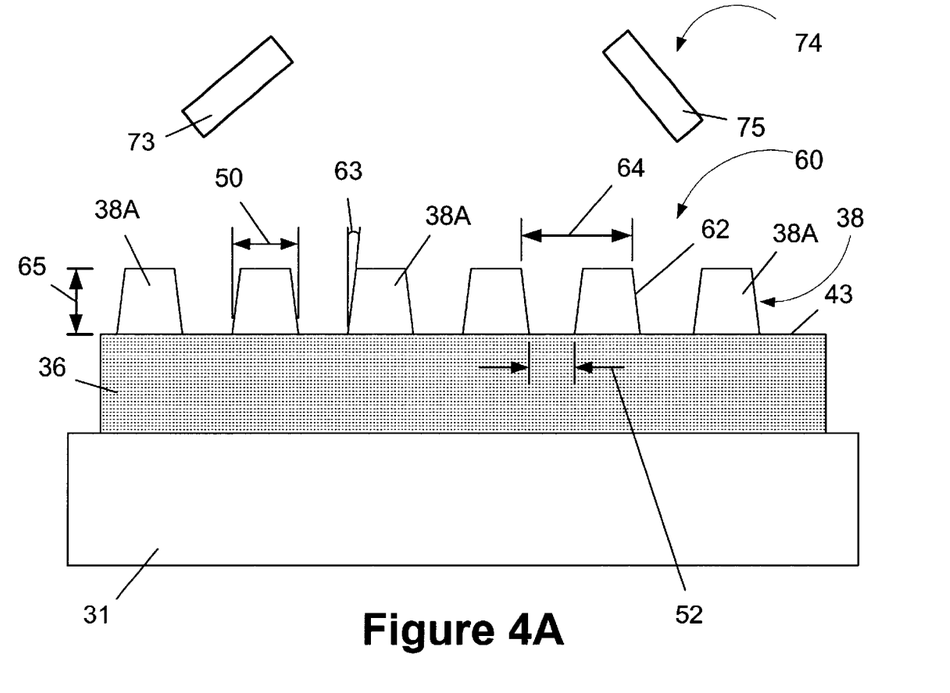
FIGS. 4A–4B depict one illustrative embodiment of an illustrative grating structure that may be employed with the present invention.
Figure 4B:
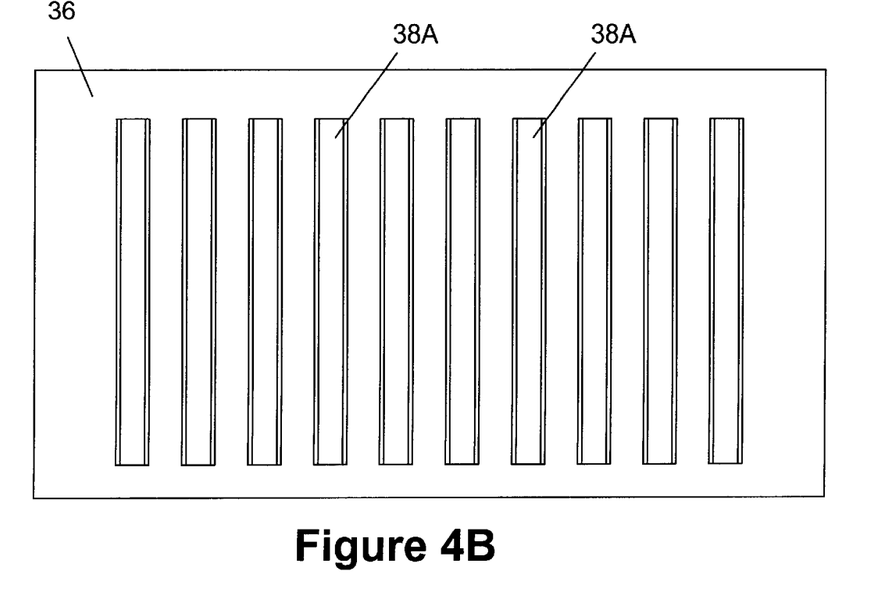

The size, shape, and configuration of the grating structures 60A–I may be varied. For example, one such illustrative grating structure 60, depicted in FIGS. 4A–4B, is comprised of a plurality of photoresist features 38A, e.g., lines, formed in a layer of photoresist 38. The layer of photoresist 38 is formed above a representative process layer 36. The photoresist features 38A comprising the grating structure 60 have a thickness 65 and sidewalls 62 disposed at an angle 63 (relative to a line normal to the surface 43 of the process layer 36). The photoresist features 38A are separated by a space 52 that defines the critical dimension of the illustrative grating structure 60. The thickness 65, the sidewall angle 63, the pitch 64 of the photoresist features 38A, and the spacing 52 between the photoresist features 38A may be varied as a matter of design choice. For example, the grating structure 60 may be formed in regions having approximate dimensions of 100 $\mu$m×120 $\mu$m, and it may be comprised of approximately 300–400 photoresist features 38A (depending upon the selected pitch). The thickness 65 of the photoresist features 38A will generally correspond to the thickness of the layer of photoresist 38.

Each of the grating structures 60A–I, or the array 61 comprising the grating structures 60, may be formed as a separate test structure that is formed in the layer of photoresist 38 in an area defined by a scribe line 42A of a wafer 31. The photoresist features 38A that are part of the grating structure 60 may be formed at the same time that other photoresist features are being formed for production devices formed on the wafer 31. That is, a pattern for the grating structure 60 may be formed in a reticle that will be used in the process of exposing the layer of photoresist 38 to form production integrated circuit devices within the die 42. Alternatively, a separate reticle may be used wherein only the grating structures 60 are formed in the layer of photoresist 38. This separate reticle may be used before or after the reticle used to expose the production devices is used.

Figure 5:
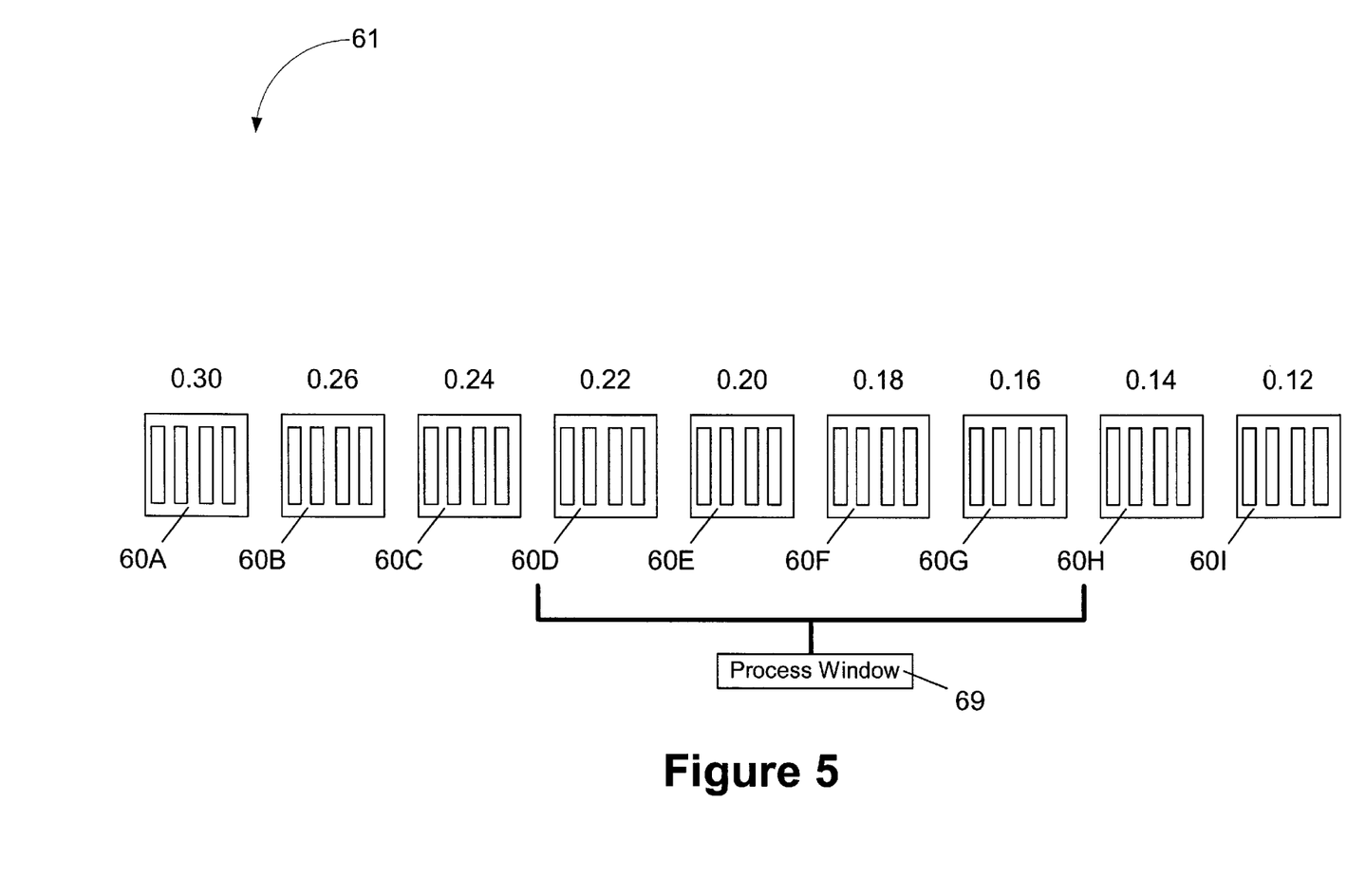
FIG. 5 is an enlarged view of an illustrative array of grating structures that may be employed with the present invention.

FIG. 5 depicts an illustrative array 61 comprised of the illustrative grating structures 60A–I. Each of the grating structures 60A–I is comprised of a plurality of photoresist features 38A. Although the pitch 64 (see FIG. 4A) of the photoresist features 38A may vary, in one illustrative embodiment of the present invention, the pitch 64 between the features 38A is essentially constant in each of the grating structures 60A–I depicted in FIG. 5. As will be understood by those skilled in the art after a complete reading of the present application, if the pitch 64 were to substantially vary, additional scatterometry libraries may be required. However, the spacing 52 between the photoresist features 38A on each grating structure 60A–I is different. That is, the photoresist pattern for each of the grating structures 60A–I has a different critical dimension. For example, as shown in FIG. 5, the grating structures 60A–I may be comprised of photoresist features 38A having a spacing 52, i.e., a critical dimension, of, respectively, 0.30 $\mu$m, 0.26 $\mu$m, 0.24 $\mu$m, 0.22 $\mu$m, 0.18 $\mu$m, 0.16 $\mu$m, 0.14 $\mu$m and 0.12 $\mu$m. The particular size of the spacing 52 between the features 38A comprising the grating structure 60A–I, the pitch 64 between the features 38A, and the incremental difference in the spacing 52 between the photoresist features 38A comprising the grating structure 60 may vary.

Typically, the spacing 52 between the features 38A comprising the various grating structures 60A–I will be such that at least some of the plurality of grating structures 60A–I will be comprised of photoresist features 38A having a spacing 52 (critical dimension) that is comparable to the intended critical dimension of features to be formed in manufacturing production devices. That is, the photoresist features 38A for these grating structures 60 will be representative of a process window 69 where the spacing 52 between the photoresist features 38A is representative of the range of critical dimension of features that will be formed on an integrated circuit device. In addition, at least some of the grating structures 60A–I will have a spacing 52 between photoresist features 38A that is less than that anticipated to be formed in manufacturing production devices. For example, as shown in FIG. 5, the grating structures 60D, 60E, 60F and 60G have critical dimensions, i.e., spacing 52, of, respectively, 0.22 $\mu$m, 0.20 $\mu$m, 0.18 $\mu$m and 0.16 $\mu$m. These four grating structures 60D–G define the illustrative process window 69. The grating structures 60H–I have critical dimensions of, respectively, 0.14 $\mu$m and 0.12 $\mu$m, sizes that are progressively less than the anticipated process window 69. The grating structures 60A–C have a spacing 52 between the photoresist features 38A of 0.30 $\mu$m, 0.28 $\mu$m, and 0.24 $\mu$m, respectively.

However, the inclusion of grating structures 60 with a spacing greater than anticipated by the process window 69 may not be required, and, thus, may be omitted in some situations. Moreover, in some situations, the grating structures that are representative of the process window 69 may be omitted. It should also be noted that, although the grating structures 60A–I are depicted as being comprised of a plurality of line-type photoresist features 38A, the photoresist features 38A may take other forms. For example, the grating structures 60A–I may be comprised of opening-type features, i.e., circular openings, wherein the critical dimension for the grating structures is defined by the diameter (or other dimension) of the opening-type features.

Photoresist scumming, or the presence of residual photoresist material between the photoresist features 38A, may be more readily detected using the plurality of grating structures 60 described herein. That is, by employing a plurality of grating structures 60, each of which have a different critical dimension, e.g., a different amount of spacing between the photoresist features 38A comprising the grating structures 60, the present invention may be used to detect and indicate when problems are occurring in photolithography processes thereby resulting in photoresist scumming. More particularly, by using a plurality of grating structures 60 wherein some of the grating structures have a spacing 52 (critical dimension) between photoresist features 38A that is less than the process window 69, the present invention may be used to detect photoresist scumming problems prior to the scumming adversely affecting the production of photoresist features to be used in forming actual production devices. Simply put, the present invention may be employed as an early warning type system that is useful in detecting the degradation of a photolithography process. For example, photolithography processes may be performed until such time as photoresist scumming is detected on the grating structures 60 having a smaller line spacing than that of the process window 69. Once detected, an appropriate instruction or indication may be provided to check one or more aspects of the photolithography process.

Ultimately, the grating structures 60A–I will be measured using scatterometric techniques, and these measurements may be used to determine the presence of residual photoresist material, i.e., photoresist scumming. Normally, these grating structures 60A–I will be formed in the layer of photoresist 38 above the space between the die 42, i.e., in the area defined by so-called scribe lines 42A. The size of the scribe lines 42A relative to the size of the die 42 in the attached figures is exaggerated for purposes of clarity. Alternatively, assuming there is available plot space, the grating structures 60A–I may be formed in the area defined by one or more of the die 42.

Figure 6:
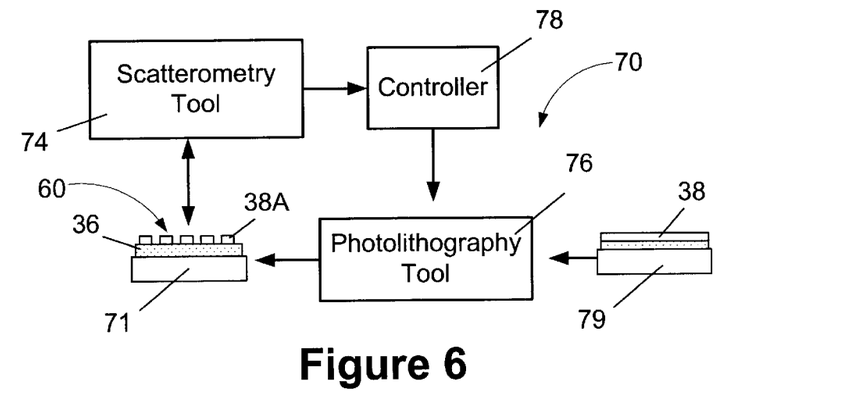
FIG. 6 depicts an illustrative embodiment of a system useful in practicing various embodiments of the present invention.

An illustrative system 70 that may be used in one embodiment of the present invention is shown in FIG. 6. The system 70 is comprised of a scatterometry tool 74, a photolithography tool 76, and a controller 78. As indicated in FIG. 6, the wafer 71 is representative of one or more wafers having a film stack comprised of at least one process layer and a layer of photoresist 38 formed thereabove. The wafer 71 is depicted at the point in the process wherein it has previously been processed in the photolithography tool 76 and has been subjected to a development process. The layer of photoresist 38 on the wafer 71 was subjected to an exposure process in a stepper tool to transfer the features defined in a reticle (not shown) to the layer of photoresist 38. During this process, the plurality of grating structures 60A–I were defined in the layer of photoresist 38, as were many other photoresist features that will be used to ultimately form production features in the underlying process layer 36. These processes result in the definition of a patterned layer of photoresist 38 that reflects the pattern in the reticle used during the exposure process. This patterned layer of photoresist 38 will be used in patterning the underlying process layer by performing one or more known etching processes.

An illustrative scatterometry tool 74 that may be used with the present invention is comprised of a representative light source 73 and a detector 75 depicted in FIG. 4A. Ultimately, the grating structures 60A–I will be measured using scatterometric techniques, and these measurements will be used to determine presence of residual photoresist material between the photoresist features 38A comprising the grating structures 60A–I. Stated another way, the scatterometry measurements can provide feedback as to the effectiveness and/or deterioration of the photolithography process.

A variety of scatterometry tools 74 may be used with the present invention, e.g., so-called 2$\theta$-type systems and lens-type scatterometry tools. The scatterometry tool 74 may use white light, or some other wavelength or combination of wavelengths, depending on the specific implementation. Typically, the scatterometry tool 74 will generate an incident beam that has a wide spectral composition and wherein the intensity of the light changes slowly in comparison to changes in wavelength. The angle of incidence of the light may also vary, depending on the specific implementation. The optical characteristic traces generated by the scatterometry tool 74 may be based upon a comparison of light intensity to wavelength (for white light, fixed angle type scatterometry tools) or a comparison of intensity to incident angle (for angle resolved systems that use a single light source). Additionally, the light source 73 and the detector 75 may be arranged in a concentric circle configuration, with the light source 73 illuminating the grating structures 60A–I from a perpendicular orientation, e.g., a reflectometer. The intensity of the reflected light may be measured as s- and p-polarization over either multiple angles or at multiple wavelengths.

In general, the scatterometry tool 74 (see FIG. 6) includes optical hardware, such as an ellipsometer or reflectometer, and a data processing unit loaded with a scatterometry software application for processing data collected by the optical hardware. For example, the optical hardware may include a Model OP5230 or OP5240 with a spectroscopic ellipsometer offered by Thermawave, Inc. of Fremont, Calif. The data processing unit may comprise a profile application server manufactured by Timbre Technologies, a fully owned subsidiary of Tokyo Electron America, Inc. of Austin, Tex. and distributed by Thermawave, Inc.

Through use of scatterometry, an optical characteristic trace for a particular grating structure 60 having a particular degree of photoresist scumming may be calculated (using Maxwell's equations and rigorous coupled wave analysis (RCWA)) for a vast variety of anticipated photoresist scumming situations for each different spacing 52 size, i.e., critical dimension, for the grating structures 60. These traces may be stored in a library. Scatterometry libraries are commercially available from Timbre Technologies, Inc. The calculated scatterometry trace may be based on a variety of characteristics of the grating structures 60A–I. For example, with reference to FIGS. 4A–4B, the optical characteristic trace may be based upon the different spacing 52 between the photoresist features 38A that comprise each of the grating structures 60. Other characteristics or combination of characteristics may also be used as the basis for the optical characteristic traces.

Variations in the amount of residual photoresist material and the associated profile degradations in the photoresist features 38A of the grating structure 60 will cause one or more of the optical characteristics of the grating structure 60 to vary. In turn, this will cause a significant change in the diffraction characteristics of the incident light from the light source 73 of the scatterometry tool 74. Thus, using Maxwell's equations, a unique optical characteristic trace may be established for a variety of anticipated situations reflecting unwanted photoresist scumming. A library of traces corresponding to each anticipated situation may be calculated and stored in a library. Through this technique, each trace in the library represents a grating structure 60 comprised of photoresist features having a known spacing 52 and a known degree or presence of unwanted residual photoresist material.

The present invention may be employed to correlate or match a measured or generated trace of a grating structure 60 comprised of a plurality of photoresist features 38A having an unknown degree of photoresist scumming to a library of such traces, each of which corresponds to a grating structure 60 having a known degree of photoresist scumming. That is, in one embodiment, the scatterometry tool 74 is used to measure and generate a trace for a given grating structure 60 comprised of a plurality of photoresist features 38A formed in a layer of photoresist 38 having an unknown degree or amount of residual photoresist material positioned between the features 38A. The scatterometry tool 74 may measure one or more of the grating structures 60 on a given wafer. The scatterometry tool 74 (or some other controller resident within the manufacturing plant, e.g., controller 78) compares the measured trace (i.e., individual or averaged) to a library of traces with known degrees of residual photoresist material to correlate or approximately match the current measured trace with a trace in the library. When a match is confirmed, the scatterometry tool 74 (or other controller) may then provide data as to the presence and/or amount or degree of residual photoresist material positioned between the features 38A of the formed grating structure 60.

Based upon these comparisons, the completeness and/or deterioration of the photo lithography process used to form one or more grating structures 60A–I, and other photoresist features, may be determined, analyzed, or evaluated. For example, with reference to FIG. 5, if the matching of the generated optical characteristic trace for the grating structure 601 indicates the presence of unwanted photoresist material, this means that the photolithography process is unable to effectively pattern features having a critical dimension of 0.12 μm or less. At this point, the photolithography process may still be able to reliably produce integrated circuit devices with features having critical dimensions within the process window 69, i.e., 0.22–0.16 μm. Subsequently, photoresist scumming may be detected on the grating structure 60H, having a critical dimension of 0.14 μm. While the photolithography process may still be able to effectively form features having critical dimensions within the process window 69, the detection of photoresist scumming on the grating structure 60H is an indication that the photolithography process is degrading. At this point, the photolithography process may be discontinued until such time as the cause of the photoresist scumming process can be identified and corrected. By way of example, it may be the case that the light source (not shown) within the stepper tool has gradually degraded over time to the point that it no longer provides the same exposure dose, even though settings on the stepper tool indicate that it should. In this situation, the light source in the stepper tool may be replaced prior to performing additional exposures processes on additional wafers. In general, the measurement of the grating structures 60 provides feedback as to the effectiveness and possible degradation of the photolithography process prior to it becoming an issue with respect to the formation of the larger photoresist features in production areas of the wafer.

In the illustrated embodiments, the controller 78 is a computer programmed with software to implement the functions described herein. Moreover, the functions described for the controller 78 may be performed by one or more controllers spread through the system. For example, the controller 78 may be a fab level controller that is used to control processing operations throughout all or a portion of a semiconductor manufacturing facility. Alternatively, the controller 78 may be a lower level computer that controls only portions or cells of the manufacturing facility. Moreover, the controller 78 may be a stand-alone device, or it may reside on the etch tool 76. However, as will be appreciated by those of ordinary skill in the art, a hardware controller (not shown) designed to implement the particular functions may also be used.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic of computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 78, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI.

The present invention is directed to various methods of detecting degradation in photolithography processes based upon scatterometric measurements of grating structures, and a device comprising such structures. In one illustrative embodiment, the method comprises providing a wafer comprised of a plurality of grating structures, each of the grating structures being comprised of a plurality of features, each of the grating structures having a different critical dimension, illuminating at least one of the grating structures, measuring light reflected off of at least one of the grating structures to generate an optical characteristic trace for the grating structure, and determining the presence of residual photoresist material between the features of the grating structure by comparing the generated optical characteristic trace to at least one optical characteristic trace from a library. In some embodiments, the grating structures are arranged in a linear array. In further embodiments, at least one and, in some cases, a plurality of grating structures have a critical dimension that is less than an anticipated range of critical dimensions for integrated circuit devices to be formed on a wafer.

In another illustrative embodiment, the method comprises providing a wafer comprised of a plurality of grating structures, each of the grating structures being comprised of a plurality of spaced-apart photoresist features, each of the grating structures having a different spacing between the photoresist features, at least one of the grating structures having a spacing between the photoresist features that is less than an anticipated range of critical dimensions for integrated circuit devices to be formed on a wafer, illuminating at least one of the plurality of grating structures, measuring light reflected off of at least one of the grating structures to generate an optical characteristic trace for the at least one grating structure, and determining the presence of residual photoresist material between the features of the at least one grating structure by comparing the generated optical characteristic trace to at least one optical characteristic trace from a library. In some embodiments, the photoresist features are line-type features.

In a further embodiment, the device comprises a wafer and a plurality of grating structures formed above the wafer, each of the grating structures having a different critical dimension, and at least one of the grating structures having a critical dimension that is less than an anticipated range of critical dimensions for integrated circuit devices to be formed on a wafer. In additional embodiments, at least two of the grating structures have a critical dimension that is less than an anticipated range of critical dimensions for integrated circuit devices that are to be manufactured on the wafer. In even further embodiments, the grating structures are arranged in a linear array.

Through use of the present invention, better process control may be achieved in modem integrated circuit manufacturing. More particularly, the present invention may enable early detection in the degradation of photolithography processes employed in manufacturing integrated circuit devices, thereby improving device performance and increasing production yields.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
   providing a wafer comprised of a plurality of grating structures, each of said grating structures being comprised of a plurality of features, each of said grating structures having a different critical dimension;
   illuminating at least one of said plurality of grating structures;
   measuring light reflected off of at least one of said grating structures to generate an optical characteristic trace for said at least one grating structure; and
   determining the presence of residual photoresist material between said features of said at least one grating structure by comparing said generated optical characteristic trace to at least one optical characteristic trace from a library.

2. The method of claim 1, wherein said plurality of grating structures are arranged in a linear array.

3. The method of claim 1, wherein at least one of said grating structures has a critical dimension that is less than an anticipated range of critical dimensions for integrated circuit devices to be formed on a wafer.

4. The method of claim 1, wherein each of said plurality of grating structures has a critical dimension that is less than an anticipated range of critical dimensions for integrated circuit devices to be formed on a wafer.

5. The method of claim 1, wherein a plurality of said grating structures have a critical dimension that is progressively less than an anticipated range of critical dimensions for integrated circuit devices to be formed on a wafer.

6. The method of claim 1, wherein at least one of said grating structures has a critical dimension that is greater than an anticipated range of critical dimensions for integrated circuit devices to be formed on a wafer.

7. The method of claim 1, wherein each of said grating structures is comprised of a plurality of photoresist features, each of said grating structures having a different critical dimension.

8. The method of claim 1, wherein said plurality of grating structures are formed in at least one scribe line of said wafer.

9. The method of claim 1, wherein said critical dimension is a spacing between said features of said grating structures.

10. A method, comprising:
   providing a wafer comprised of a plurality of grating structures arranged in a linear array, each of said grating structures being comprised of a plurality of photoresist features, each of said grating structures having a different critical dimension;
   illuminating at least one of said plurality of grating structures;
   measuring light reflected off of at least one of said grating structures to generate an optical characteristic trace for said at least one grating structure; and
   determining the presence of residual photoresist material between said features of said at least one grating structure by comparing said generated optical characteristic trace to at least one optical characteristic trace from a library.

11. The method of claim 10, wherein at least one of said grating structures has a critical dimension that is less than an anticipated range of critical dimensions for integrated circuit devices to be formed on a wafer.

12. The method of claim 10, wherein at least some of said plurality of grating structures have a critical dimension that is less than an anticipated range of critical dimensions for integrated circuit devices to be formed on a wafer.

13. The method of claim 10, wherein a plurality of said grating structures have a critical dimension that is progressively less than an anticipated range of critical dimensions for integrated circuit devices to be formed on a wafer.

14. The method of claim 10, wherein at least one of said grating structures has a critical dimension that is greater than an anticipated range of critical dimensions for integrated circuit devices to be formed on a wafer.

15. The method of claim 10, wherein said plurality of grating structures arranged in a linear array are formed in at least one scribe line of said wafer.

16. The method of claim 10, wherein said critical dimension is a spacing between said features of said grating structures.

17. A method, comprising:
   providing a wafer comprised of a plurality of grating structures, each of said grating structures being comprised of a plurality of spaced-apart photoresist features, each of said grating structures having a different spacing between said photo-resist features, at least one of said grating structures having a spacing between said photoresist features that is less than an anticipated range of critical dimensions for integrated circuit devices to be formed on a wafer;
   illuminating at least one of said plurality of grating structures;
   measuring light reflected off of at least one of said grating structures to generate an optical characteristic trace for said at least one grating structure; and
   determining the presence of residual photoresist material between said features of said at least one grating structure by comparing said generated optical characteristic trace to at least one optical characteristic trace from a library.

18. The method of claim 17, wherein said plurality of grating structures are arranged in a linear array.

19. The method of claim 17, wherein each of said plurality of grating structures has a spacing between said photoresist features that is less than an anticipated range of critical dimensions for integrated circuit devices to be formed on a wafer.

20. The method of claim 17, wherein a plurality of said grating structures have a spacing between said photoresist features that is progressively less than an anticipated range of critical dimensions for integrated circuit devices to be formed on a wafer.

21. The method of claim 17, wherein at least one of said grating structures has a spacing between said photoresist features that is greater than an anticipated range of critical dimensions for integrated circuit devices to be formed on a wafer.

22. The method of claim 17, wherein said plurality of grating structures are formed in at least one scribe line of said wafer.

23. A method, comprising:
   providing a wafer comprised of a plurality of grating structures arranged in a linear array, each of said grating structures being comprised of a plurality of features, each of said grating structures having a different critical dimension, at least one of said grating structures having a critical dimension that is less than an anticipated range of critical dimensions for integrated circuit devices to be formed on a wafer;
   illuminating at least one of said plurality of grating structures;
   measuring light reflected off of said at least one grating structure to generate an optical characteristic trace for said at least one grating structure; and
   determining the presence of residual photoresist material between said features of said at least one grating structure by comparing said generated optical characteristic trace to at least one optical characteristic trace from a library.

24. The method of claim 23, wherein said at least one grating structure having a critical dimension that is less than an anticipated range of critical dimensions for integrated circuit devices to be formed on a wafer comprises a plurality of grating structures having a critical dimension that is less than said anticipated range of critical dimensions for integrated circuit devices to be formed on a wafer.

25. The method of claim 23, wherein at least one of said grating structures has a critical dimension that is greater than an anticipated range of critical dimensions for integrated circuit devices to be formed on a wafer.

26. The method of claim 23, wherein each of said grating structures have a different critical dimension.

27. The method of claim 23, wherein said plurality of grating structures are arranged in a linear array formed in at least one scribe line of said wafer.

28. The method of claim 23, wherein said critical dimension is a spacing between said features of said grating structures.

29. A device, comprising:
   a wafer; and
   a plurality of grating structures formed above said wafer, each of said grating structures having a different critical dimension, at least one of said grating structures having a critical dimension that is less than an anticipated range of critical dimensions for integrated circuit devices to be formed on a wafer.

30. The device of claim 29, wherein said wafer is comprised of at least one of silicon and gallium arsenide.

31. The device of claim 29, wherein said plurality of grating structures are arranged in a linear array.

32. The device of claim 31, wherein said linear array of grating structures is formed in a scribe line of said wafer.

33. The device of claim 29, wherein said grating structures are comprised of a plurality of photoresist features.

34. The device of claim 33, wherein said critical dimension of said grating structure is defined by a spacing between said photoresist features.

35. The device of claim 29, wherein at least two of said plurality of grating structures have a critical dimension that is less than said anticipated range of critical dimensions for integrated circuit devices to be formed on said wafer.

36. The device of claim 29, wherein at least some of said plurality of grating structures have critical dimensions that are representative of said anticipated range of critical dimensions for integrated circuit devices to be formed on said wafer.

37. The device of claim 29, wherein at least one of said plurality of grating structures has a critical dimension that is greater than said anticipated range of critical dimensions for integrated circuit devices to be formed on said wafer.

38. The device of claim 29, wherein at least some of said grating structures are formed in a scribe line of said wafer.

39. A device, comprising:
   a wafer; and
   a plurality of grating structures formed above said wafer, each of said grating structures being comprised of a plurality of photoresist features, each of said grating structures having a different critical dimension, at least two of said grating structures having a critical dimension that is less than an anticipated range of critical dimensions for integrated circuit devices to be formed on a wafer.

40. The device of claim 39, wherein said wafer is comprised of at least one of silicon and gallium arsenide.

41. The device of claim 39, wherein said plurality of grating structures are arranged in a linear array.

42. The device of claim 41, wherein said linear array of grating structures is formed in a scribe line of said wafer.

43. The device of claim 39, wherein at least some of said plurality of grating structures have critical dimensions that are representative of said anticipated range of critical dimensions for integrated circuit devices to be formed on said wafer.

44. The device of claim 39, wherein at least one of said plurality of grating structures has a critical dimension that is greater than said anticipated range of critical dimensions for integrated circuit devices to be formed on said wafer.

45. The device of claim 39, wherein at least some of said grating structures are formed in a scribe line of said wafer.

46. The device of claim 39, wherein said critical dimension of said grating structure is defined by a spacing between said photoresist features.

* * * * *